United States Patent [19]

Scherer

[11] 4,409,565

[45] Oct. 11, 1983

[54] CIRCUIT ARRANGEMENT FOR PRODUCING A LOW FREQUENCY ALTERNATING CURRENT

[76] Inventor: Erich Scherer, Wiesenstrasse 18, D-6603 Sulzbach, Fed. Rep. of Germany

[21] Appl. No.: 234,931

[22] Filed: Feb. 17, 1981

[30] Foreign Application Priority Data

Feb. 29, 1980 [DE] Fed. Rep. of Germany ....... 3007717

[51] Int. Cl.³ .................. H03B 21/01; A61N 1/36
[52] U.S. Cl. .................. 331/40; 128/422; 331/48; 331/56
[58] Field of Search .......... 331/46, 48, 56, 37, 331/40; 128/421, 422

[56] References Cited

U.S. PATENT DOCUMENTS

| | | | |
|---|---|---|---|
| 3,523,255 | 8/1970 | Rhyne, Jr. et al. | 331/56 |
| 3,564,447 | 2/1971 | Chase | 331/56 X |
| 4,249,537 | 2/1981 | Lee et al. | 128/422 |

FOREIGN PATENT DOCUMENTS 2545675 4/1976 Fed. Rep. of Germany .

OTHER PUBLICATIONS

"Elektrotherapie" by Otto Gillert, Published by: Pflaum Verlag Muenchen; pp. 108 and 109.

Primary Examiner—Siegfried H. Grimm
Attorney, Agent, or Firm—W. G. Fasse; D. H. Kane, Jr.; D. F. Gould

[57] ABSTRACT

The invention relates to a circuit arrangement for producing a low frequency alternating current, such as is particularly used for electric massaging. Any desired frequency characteristics and beats may be produced by the interconnecting of several generators having different, adjustable fundamental frequencies, and by an adjustability of the coupling components. These frequency characteristics and beats have proven to be particularly effective. Above all, the components of the line frequencies of 50-60 Hz, which are dangerous to the human body, are avoided.

11 Claims, 10 Drawing Figures

CIRCUIT ARRANGEMENT FOR PRODUCING A LOW FREQUENCY ALTERNATING CURRENT

BACKGROUND OF THE INVENTION

The invention relates to a circuit arrangement for producing a low frequency alternating current, the frequency of which is to be adjustable within the range of about 0–100 Hz.

Circuit arrangements of this type are used in electric massaging devices.

In a known circuit arrangement, a low frequency alternating current is produced and the normal line frequency of 50 Hz is superimposed on said low frequency alternating current so that a time-dependent increase and decrease in the amplitude is attained. Voltage peaks, which in spite of the existing attenuation may pose a threat to the patient, may occur as a result of disturbances in the line voltage during gating through a transformer. An additional disadvantage of such a known circuit arrangement is seen in that the frequency of the amplitude which varies as a function of time and the oscillation curve or the shape of the oscillation curve are not controllable as desired.

OBJECTS OF THE INVENTION

It is thus the aim of this invention to provide a circuit arrangement of the type described above, which circuit arrangement not only makes possible a desired controlling of the changing frequency and of the shape of the oscillation curve, but which additionally produces a wide harmonic waveband.

SUMMARY OF THE INVENTION

The invention provides, in order to achieve this stated aim, that more than two generators, driven by 12–15 volts direct current, are connected in parallel and to a common output; and that each of said generators produces an alternating current with a fundamental frequency of about 4000 Hz, wherein said generators modulate said alternating current by means of different superimposed frequencies, and wherein said generators are coupled by means of transformers to a common output, which comprises the superimposed modulation frequencies of the generators.

A further embodiment of the invention provides that each generator comprises additional oscillation circuits for producing harmonic waves and a regenerative circuit coupled back to the input.

Each generator also comprises an input potentiometer for controlling the operating point. The invention provides additionally that each generator has an output oscillation circuit which comprises a potentiometer and a transformer connected in parallel to said potentiometer. This arrangement is thus advantageously such that the input potentiometer is a component of the output oscillation circuit.

BRIEF FIGURE DESCRIPTION

In the following the invention is described in more detail by way of example with reference to the drawings, wherein.

DETAILED DESCRIPTION OF PREFERRED EXAMPLE EMBODIMENTS AND OF THE BEST MODE OF THE INVENTION

Figure 1:
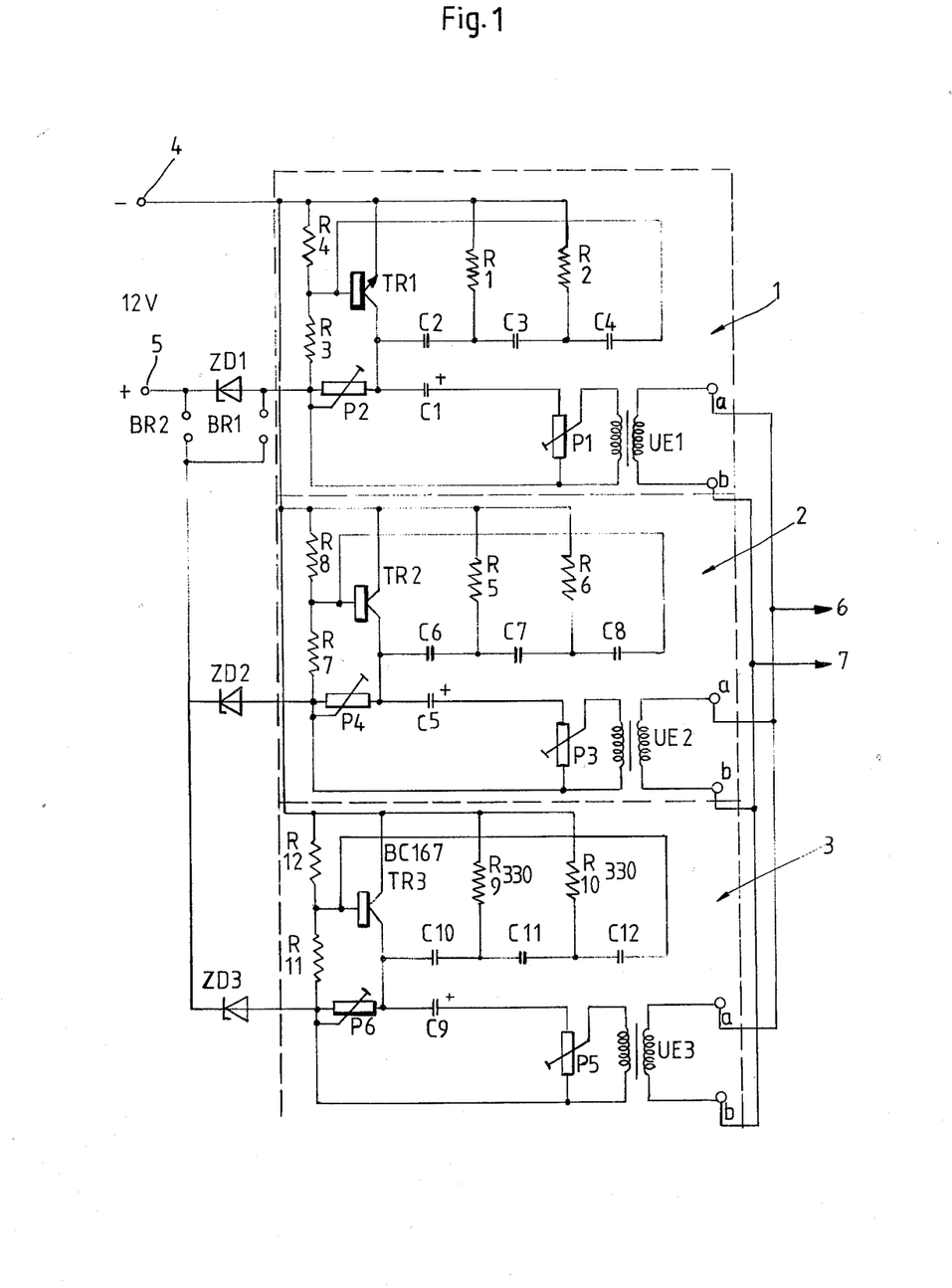
FIG. 1 shows a circuit diagram of a preferred example embodiment.

The circuit diagram of FIG. 1 shows three alternating current sine wave generators 1, 2, and 3, each of which is connected to the input terminals 4 and 5 by means of Zener diodes ZD 1 to ZD 3. An input voltage of 12 volts, for example, is applied to the input terminals.

A transistor TR 1 is driven by means of a voltage divider R3 to R4. The operating point of the transistor TR1 is controllable by means of a potentiometer P2. An oscillating circuit comprising a resistor R1 and a capacitor C2, is connected to the emitter and collector of the transistor. A second oscillating circuit comprising the resistor R2 and the capacitor C3 is connected parallel to this first oscillating circuit. A capacitor C4 is connected to this second oscillating circuit and in turn connected to the base of the transistor TR1.

Harmonic waves are produced by means of variously dimensioning of the first and second oscilating circuits and the regenerative feed back circuit with the capacitor C4 modulates the produced oscillation which is available at the output circuit. This output circuit comprises, in addition to the already mentioned potentiometer P2, a capacitor C1 and a potentiometer P1.

A transformer UE1 parallel to the potentiometer P1 is connected to the output lines 6 and 7.

Figure 2:
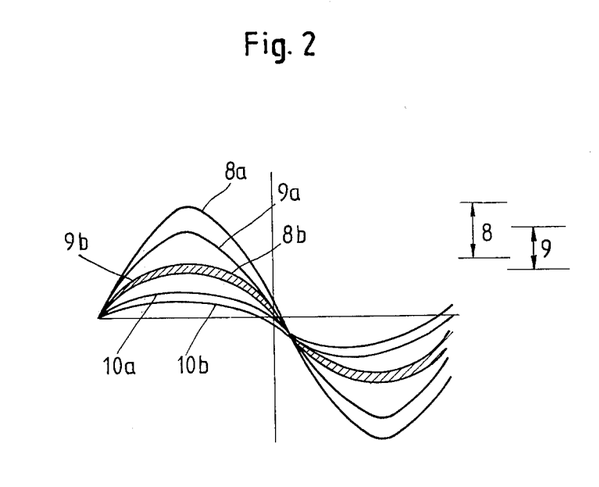
FIG. 2 shows purely schematically the outputs of the individual generators.
Figure 2A:
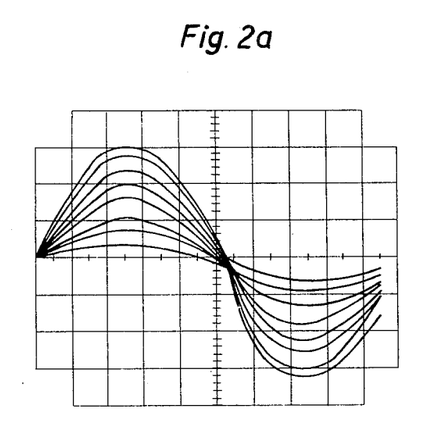
FIG. 2a shows a photograph of the corresponding oscilloscope image.

The generators 2 and 3 correspond substantially to the arrangement of the generator 1. However, the generators 2 and 3 have in turn differently dimensioned components. FIG. 2 illustrates purely schematically the output of the three generators. Accordingly, generator 1, for example, delivers a number of sine wave oscillations which fall between the envelope curves 8a and 8b. The generator 2 delivers oscillations which fall between the envelopes 9a and 9b, while the oscillations of the generator 3 fall between the envelopes 10a and 10b.

It can be seen that the frequencies of the oscillations of the generators are different and also that the oscillations produced by a single generator vary within a particular frequency range. A time dependent change in the amplitudes of the oscillations of generator 1 within the region designated by reference number 8 in FIG. 2 thus occurs while the amplitudes of the oscillations of generator 2 vary within the region designated by reference number 9. This time dependent change is brought about by the addition of the oscillations at the linked outputs of the generators.

Figure 3:
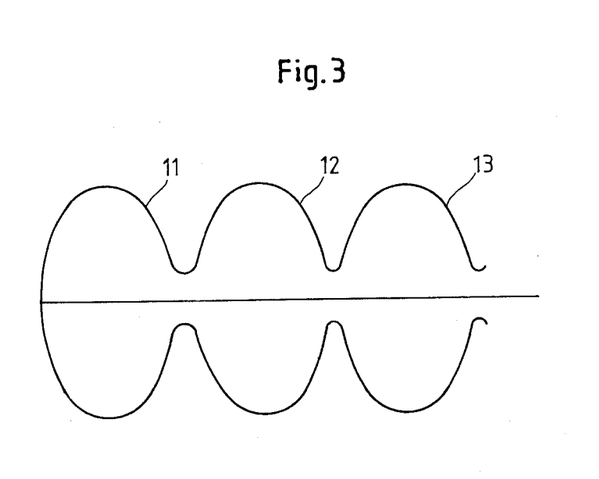
FIG. 3 shows the envelope curves of the unmodulated output voltage.

By pure summing or addition, oscillations, the envelopes of which are designated in a static condition in FIG. 3 by reference number 11, thus result from a fundamental frequency of 4000 Hz.

Appropriate adjustment of the output potentiometers P1, P3 and P5 provides time dependent changes in the amplitudes of the oscillations. These time dependent amplitude changes may be interpreted as beats, whereby the beat frequency is varied by these output potentiometers $P_1$, $P_2$, $P_3$. It may be seen from FIG. 4, that the neighboring antinodes 11 and 12 of the illustration of FIG. 3 change as a function of time in such a manner such that initially the amplitude of the antinode 11, for example, becomes smaller so that the full line changes into the dashed line curve and then into the dotted line curve. The oscillation node 13 is simultaneously displaced. After reaching a minimum, the amplitude of the antinode 11 increases again while the amplitude of the antinode 12 decreases until the second end position illustrated as a dash-dotted line is reached. This amplitude variation is designated in FIG. 4 by reference number 14.

Figure 5:
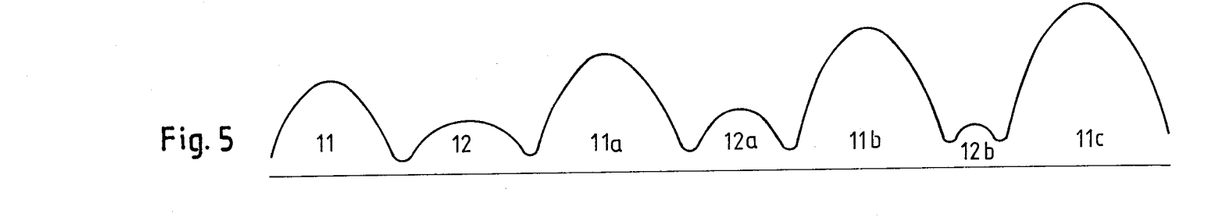
FIG. 5 shows an expanded representation for explaining FIG. 4.

FIG. 5 shows, for example, a few consecutive oscilloscope photographs of the antinodes or envelope curves 11 and 12, which have been joined next to each other for clarity.

The amplitudes of the envelope curves 11, 12 are thus modulated by beats having a beat frequency which may be varied within a range from 0 to 100 Hz by the output potentiometers $P_1$, $P_2$, $P_3$. The illustrated amplitudes correspond at their maximum to a potential of 12 volts and may be adjusted within a range of 2 to 12 volts by means of a control resistor connected to the output of the entire circuit arrangement.

It is, however, also possible to automatically control the changing frequency and/or the amplitude of the oscillations. An example embodiment for this purpose is illustrated purely schematically in FIG. 6.

Figure 6:
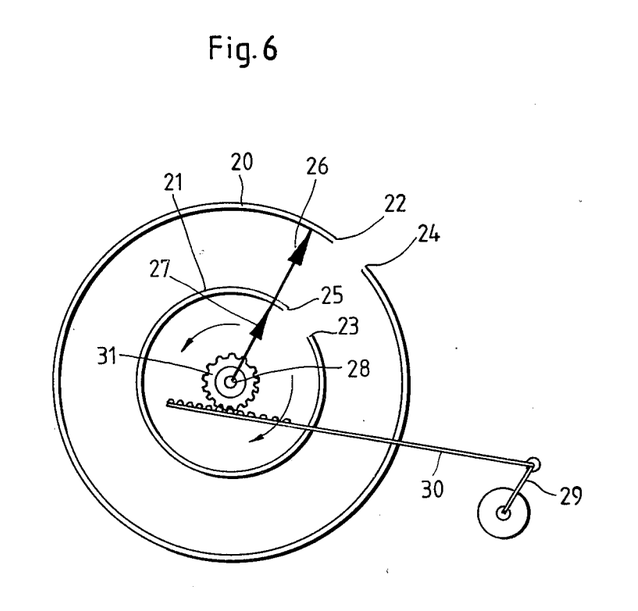
FIG. 6 shows a mechanical, automatic control apparatus for the potentiometers.

FIG. 6 shows a variable resistor with two resistive paths 20 and 21. The input to the resistive path 20 is denoted by reference number 22 and the input to the resistive path 21 is denoted by reference number 23. The output of the resistive path 20 is denoted by reference number 24, and the output of the resistive path 21 is denoted by reference number 25.

It is thus clear that by rotating the wiper arms 26 and 27, which are connected to a common terminal 28, in one direction, the resistance of the outer path increases, while the resistance of the inner path simultaneously decreases.

A crank drive 29, for example, may be provided in order to fully automatically move the wiper arms in one direction or the other. A toothed rack 30 cooperating with a drive pinion 31 is pivotally connected to the crank of the crank drive 29.

An apparatus for producing alternating currents for electrotherapy is known from the German Patent Publication DE-OS No. 25 45 675, wherein three generators each produce an alternating current each of which is connected to a respective pair of electrodes. For example, one of the generators produces a frequency of 4000 Hz, the second generator produces a frequency between 4050 and 4100 Hz, while the third generator produces a frequency, which only differs from 4000 Hz by a very slight value. The six electrodes which are applied to the body produce among themselves an electromagnetic field, which is supposed to form interferences.

Other known generators for producing currents for electrotherapy are constructed so that individual impulses are produced which have a substantially triangular shape and which furthermore have a short impulse duration and in relation thereto relatively large impulse spacings. The impulse frequency is precisely adjustable in such generators. These known generators operate, as mentioned above, on the input side with the line frequency and comprise output transformers. Because of the use of line frequency, voltage peaks or current peaks may be produced by inductive transformation. The values of these voltage peaks or current peaks may be dangerous for electrotherapeutic treatment.

In addition to this, the impulses produced by the known generators are pure peak impulses, the effect of which corresponds to the effect of a current shock therapy.

Contrary thereto, with the above described invention, a voltage pattern is produced as an output of the generator circuit which constantly maintains the original sinusoidal shape. No voltage peaks or current peaks occur.

This is brought about primarily by the high proportion of harmonic waves in the output signals of the individual generators.

Consequently, no output frequencies are formed which are adjustable to a fixed value. Rather only adjustable output frequency ranges are formed, such as, for example, from 5 to 20 Hz. Only the average value of these output frequency ranges is constant to some degree. Each of the modulating frequencies may be shifted up to about 300 Hz by means of adjusting the input potentiometers, (P2, P4, and P6,) of the generators 1, 2, 3. Beats result from the superimposition of the outputs of three generators. The best frequency ranges of these beats are adjustable between 0-100 Hz by the output potentiometers $P_1$, $P_3$, $P_5$ and these beats replace the defined output impulses of the known generators.

A component chart with the dimensions of the individual components for a preferred example embodiment of the invention is set forth below.

The curves shown in FIGS. 2-5 were obtained with these components forming the circuit arrangement according to FIG. 1.

The critical characteristic of the current path or of the voltage path according to the invention is to be seen in that the amplitudes change continuously, and in that the oscillation nodes 13 lie close to the zero line. Because of these characteristics, each time an oscillation or vibration node is sensed by a treated body zone, a relieving of the body cells is attained. Massaging by hand is nearly simulated in this manner.

In this connection, the fundamental frequency of 4000 Hz of the output current however is basically maintained. Only the frequencies defined by the envelope curves and varying simultaneously with the beat frequency comprise the effective portion of the current acting on the body. The intensity of these frequencies is relatively small and also adjustable.

Figure 7:
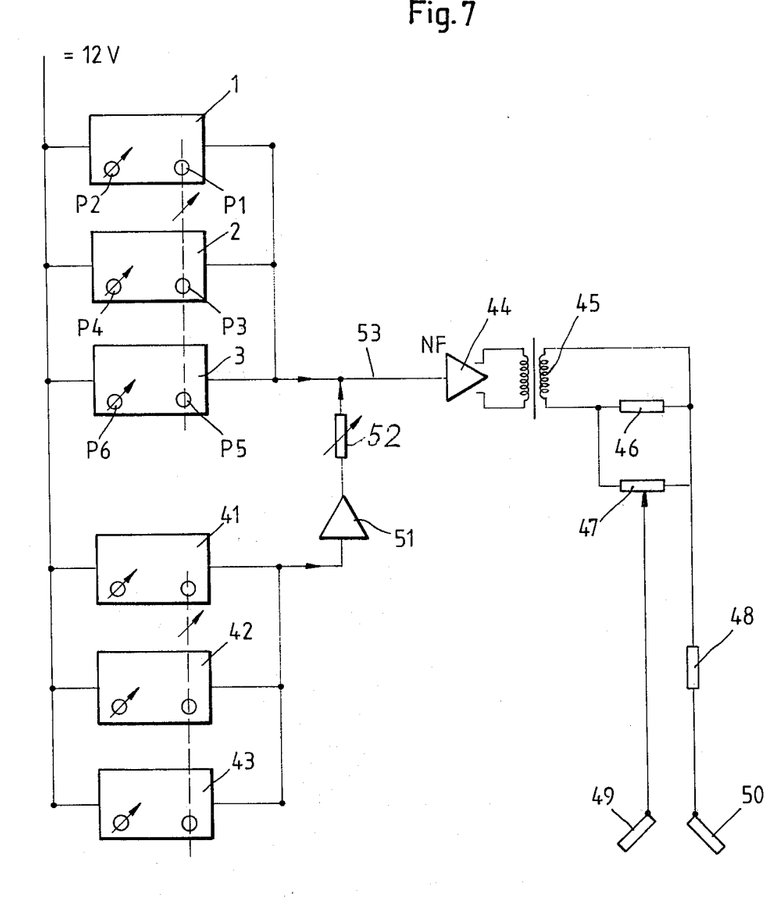
FIG. 7 shows a circuit arrangement according to one embodiment of the invention.

Another particularly advantageous embodiment of the invention is illustrated in FIG. 7 in the form of a block diagram.

The three generators 1, 2, and 3 in FIG. 7 correspond to the generators of FIG. 1. The adjustable potentiometers P2, P4, and P6 in this instance are illustrated once more separately. The potentiometers P1, P3, and P5 are coupled to one another by means of an arrangement according to FIG. 6.

A group of three generators 41, 42, and 43 is connected in parallel to the input of the above three generators. The construction of the generators 41, 42, and 43 corresponds completely to the construction of the generators according to FIG. 1.

The outputs of the first group of generators 1, 2, 3 are connected at a common output 53. This output 53 feeds a low frequency amplifier 44, the output of which is connected to a transformer 45. The secondary side of the transformer 45 comprises a load resistor 46 and a potentiometer 47 for adjusting the output voltage. The output also comprises another load resistor 48. Both output conductors are connected to electrodes 49 and 50 known as such.

According to a further embodiment on the invention, the three generators 41, 42, and 43 are connected to a pre-amplifier 51, which serves simultaneously as a decoupler. This pre-amplifier prevents the output of the mutually influencing generators 1, 2, and 3 from also affecting the generators 41, 42, and 43.

The output of the pre-amplifier 51 is connected to the output circuit 53 of the first generator group by means of a variable resistor 52.

Figure 4:
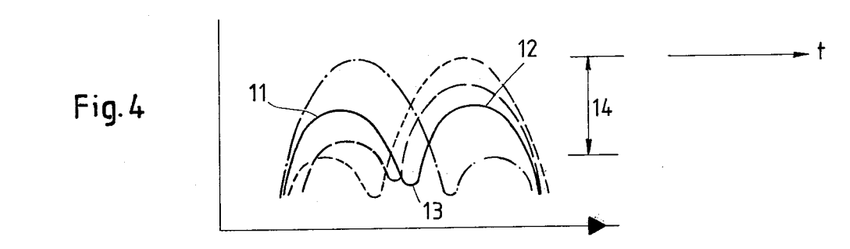
FIG. 4 shows the time dependent successive changing of the envelope curves after a respective modulation.
Figure 8:
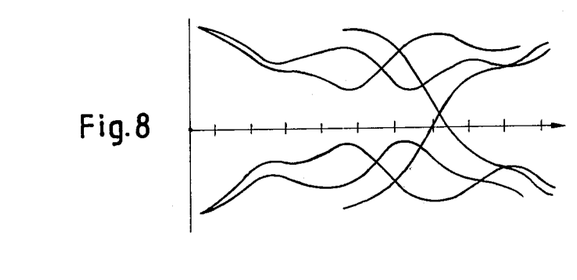
FIG. 8 shows purely schematically the output of the circuit arrangement of FIG. 7.
Figure 8A:
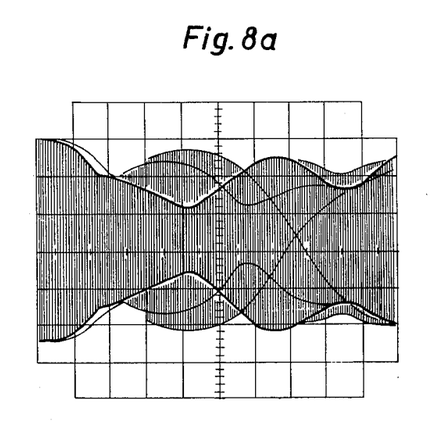
FIG. 8a shows a photograph of the corresponding oscilloscope image.

The envelope curve of the output signal at the electrodes 49 and 50 is illustrated purely schematically as an example in FIG. 8. This illustration corresponds substantially to what is shown in FIG. 4; that is, the drawing shows a segment of the current characteristic or of the voltage characteristic time. The longest wave length portion of the beat curve in the illustration of FIG. 8 corresponds to a frequency of about 100 Hz, while the shortest wave length portion corresponds to a frequency of about 12 Hz. The beat frequency itself in this instance is somewhat below 100 Hz.

The superposition of the outputs of both genertor groups is clearly noticeable in the drawing of FIG. 8. The superposition leads to further amplitude modulations in the shorter wave length region of the characteristic curve.

It should be mentioned here again, that these envelopes curves as well as the envelope curves of FIGS. 3–5 comprise the intermediate frequency portion of oscillations of 4000 Hz.

Mention is made here, regarding the practical embodiment of a circuit arrangement according to the invention, that the potentiometers P2, P4, and P6 and the corresponding potentiometers of the second generator group may be adjusted using tabulated values and that the setting of the resistors 52 and 47 are adjusted according to the individual needs and the tolerance of a patient.

| LIST OF COMPONENTS FOR THE CIRCUIT BOARD | |
|---|---|
| $R_1 = 470 \Omega$ | $C_1 = 4.7 \mu F$ |
| $R_2 = 470 \Omega$ | $C_2 = 33 n$ |
| $R_3 = 33 k\Omega$ | $C_3 = 33 n$ |
| $R_4 = 6.8 k\Omega$ | $C_4 = 22 n$ |
| $R_5 = 390 \Omega$ | $C_5 = 4.7 \mu$ |
| $R_6 = 390 \Omega$ | $C_6 = 33 n$ |
| $R_7 = 33 k\Omega$ | $C_7 = 33 n$ |
| $R_8 = 6.8 k\Omega$ | $C_8 = 33 n$ |
| $R_9 = 330 \Omega$ | $C_9 = 4.7 \mu$ |
| $R_{10} = 330 \Omega$ | $C_{10} = 33 n$ |
| $R_{11} = 33 k\Omega$ | $C_{11} = 33 n$ |
| $R_{12} = 6.8 k\Omega$ | $C_{12} = 47 n$ |
| $P_1 = 10 k\Omega$ | ZD 1 to 3 = 6 V |
| $P_2 = 1 k\Omega$ | UE 1 to 3 = St 855 |
| $P_3 = 10 k\Omega$ | TR 1 to 3 = BC 167 |
| $P_4 = 1 k\Omega$ | |
| $P_5 = 10 k\Omega$ | |
| $P_6 = 1 k\Omega$ | |

Although the invention has been described with reference to specific example embodiments, it will be appreciated, that it is intended to cover all modifications and equivalents within the scope of the appended claims.

What is claimed is:

1. An apparatus including a circuit arrangement for producing a low frequency alternating output current having a frequency within the range of 0 to 100 Hz comprising at least three sine wave oscillation generators (1, 2, 3) each producing a basic oscillation having a fundamental frequency of about 4000 Hz, direct current power supply means operatively connected to said sine wave oscillation generators for supplying d.c. power to said generators, common generator output terminals (6, 7) operatively connected in parallel to all three generators for providing said output current in the form of low frequency beats, each generator comprising a plurality of oscillation circuits ($R_1$, $C_2$; $R_2 k$ $C_3$) for producing different harmonic modulating frequency signals for modulating said basic oscillation, a regenerative feedback circuit ($C_4$, $C_8$, $C_{12}$) operatively connecting its respective oscillation circuits to the input of its oscillation generator for said modulating of the basic oscillation, each generator further comprising an input circuit including an input potentiometer ($P_2$, $P_4$, $P_6$) operatively connected to the input of the respective generator for varying said modulating frequency signals by varying the operating point of its respective generator, output means (49, 50), and low frequency amplifier means (44) operatively connected between said common generator output terminals and said output means, whereby said output means are supplied with said low frequency output current having the frequency of said beats.

2. The apparatus of claim 1, wherein said output means (49, 50) comprise electrodes for contacting a human body.

3. The apparatus of claim 1, wherein each sine wave generator comprises an oscillation output circuit including an output potentiometer ($P_1$, $P_3$, $P_5$) and a transformer connected in parallel to each other, said output potentiometer permitting adjustment of said low frequency beats and thus the frequency of said output current.

4. The apparatus of claim 3, wherein said input potentiometers are connected in common to said input circuit and to said output circuit.

5. The apparatus of claim 3, wherein said input potentiometer and said output potentiometer comprise a common wiper arm for adjustment in unison.

6. The apparatus of claim 3, wherein said input potentiometer and said output potentiometer comprise a common drive for adjustment in unison.

7. The apparatus of claim 3, further comprising adjustable resistor means (47) and fixed resistor means operatively connected between said transformer (45) and said output means (49, 50), and a load resistor (46) connected in parallel to the output side of said transformer (45).

8. The apparatus of claim 1, wherein said at least three oscillation generators form a first group of generators, said apparatus further comprising a second generator group (41, 42, 43) arranged in parallel to said first generator group (1, 2, 3); said second generator group also having a common output means, and decoupler amplifier means (51) operatively connecting said common output means to the common output terminals of said first generator group.

9. The apparatus of claim 1, wherein said input potentiometers ($P_2$, $P_4$, $P_6$) are combined to a single unit for a common adjustment.

10. the apparatus of claim 3, wherein said output potentiometers ($P_1$, $P_3$, $P_5$) are combined to a single unit for a common adjustment.

11. The apparatus of claim 1, wherein said direct current power supply means provide a d.c. voltage of 12 to 15 volts.

* * * * *